United States Patent [19]

Begley et al.

[11] Patent Number: 5,021,322
[45] Date of Patent: Jun. 4, 1991

[54] PHOTOGRAPHIC ELEMENT COMPRISING A DEVELOPMENT INHIBITOR RELEASING COMPOUND HAVING A LINKING GROUP BETWEEN THE CARRIER AND THE INHIBITOR

[75] Inventors: William J. Begley, Webster; Teh-Hsuan Chen, Fairport, both of N.Y.

[73] Assignee: Eastman Kodak Company, Rochester, N.Y.

[21] Appl. No.: 483,602

[22] Filed: Feb. 22, 1990

[51] Int. Cl.$^5$ .................... G03C 7/305; G03C 8/00; G03C 7/34; G03C 7/36
[52] U.S. Cl. .................... 430/223; 430/544; 430/553; 430/557; 430/957
[58] Field of Search ........... 430/223, 544, 957, 553, 430/557, 219

[56] References Cited

U.S. PATENT DOCUMENTS

| | | | |
|---|---|---|---|
| 3,227,554 | 1/1966 | Barr et al. | 430/544 |
| 4,248,962 | 2/1981 | Lau | 430/382 |
| 4,409,323 | 10/1983 | Sato et al. | 430/544 |
| 4,554,243 | 11/1985 | Ono et al. | 430/223 |
| 4,840,884 | 6/1989 | Mooberry et al. | 430/557 |
| 4,857,440 | 8/1989 | Begley et al. | 430/382 |
| 4,857,440 | 8/1989 | Begley et al. | 430/382 |
| 4,861,701 | 8/1989 | Burns et al. | 430/543 |

FOREIGN PATENT DOCUMENTS 1156127 7/1986 Japan .................... 430/544

OTHER PUBLICATIONS

*Research Disclosure*, Dec. 1989, Item #308119.

Primary Examiner—Charles L. Bowers, Jr.
Assistant Examiner—Lee C. Wright
Attorney, Agent, or Firm—Richard E. Knapp

[57] ABSTRACT

Photographic compound (A) capable of releasing a development inhibitor group by means of a displacement reaction enables increased image acutance when the compound contains in a coupling position a coupling-off group represented by the formula:

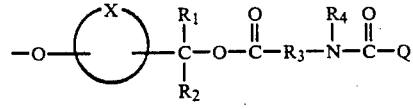

wherein X, $R_1$, $R_2$, $R_3$, $R_4$, and Q are as defined in the application. Such a compound (A) is useful in a photographic silver halide material and process.

6 Claims, No Drawings

PHOTOGRAPHIC ELEMENT COMPRISING A DEVELOPMENT INHIBITOR RELEASING COMPOUND HAVING A LINKING GROUP BETWEEN THE CARRIER AND THE INHIBITOR

This invention relates to a photographic compound that releases a development inhibitor group by means of a displacement reaction during photographic processing to enable increased image acutance and to photographic materials and processes using such a compound.

Various ways are recognized in the photographic art for releasing a development inhibitor group from a compound, such as a coupler, in a photographic material and process. For example, U.S. Pat. No. 4,248,962 describes compounds that release a photographically useful group, such as a development inhibitor group, by means of an intramolecular nucleophilic displacement reaction in photographic materials. Other examples of compounds, particularly couplers, that are capable of release of development inhibitor groups are described in U.S. Pat. Nos. 4,409,323 and 4,861,701. These compounds, particularly couplers, are capable of releasing a development inhibitor group in a photographic material upon processing with a degree of control over timing and rate of release as well as the rate and distance of diffusion of the development inhibitor group in the photographic material.

A need has existed for a compound preferably a coupler, that not only provides the described release of a development inhibitor group, but also provides increased acutance for the image provided upon processing the photographic material containing the compound. Moreover, such a need has existed with the added parameter that such a compound must not require significantly modifying the development inhibitor groups or the carrier compound, such as the couplers, in such a way that would adversely affect the ultimate end use for which each is intended.

The present invention solves this problem by means of a photographic element comprising a support bearing at least one photographic silver halide emulsion layer and at least one development inhibitor releasing compound (A) represented by the formula CAR—LINK—Q where CAR is a carrier moiety, preferably a coupler moiety, capable of releasing LINK—Q during photographic processing upon reaction with oxidized developing agent; LINK—Q is in turn capable of releasing a development inhibitor group (Q) by a displacement reaction; and LINK—Q is represented by the formula:

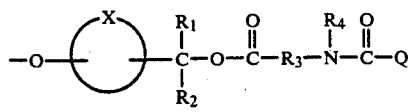

wherein

X represents the atoms, particularly atoms selected from carbon, hydrogen, nitrogen and sulfur atoms, necessary to complete an unsubstituted or substituted arylene, preferably phenylene, or heterocyclic group, preferably a 5 or 6 member ring heterocyclic group containing carbon and nitrogen atoms;

$R_1$ and $R_2$ individually are hydrogen, unsubstituted or substituted alkyl, such as alkyl containing 1 to 40 carbon atoms, or aryl, or together can complete a 5-, 6- or 7-member ring system, particularly a spiro system;

$R_3$ is a divalent group that enables formation of a ring, such as a 5-, 6- or 7-member ring, upon processing of the photographic element, preferably by means of an intramolecular nucleophilic displacement reaction;

$R_4$ is hydrogen, unsubstituted or substituted alkyl, cycloalkyl, heterocyclic, or aryl or $R_3$ and $R_4$ together can complete a ring system, such as a 5-, 6- or 7-member ring; and, Q is a releasable development inhibitor group; wherein the LINK enables formation of an image upon processing the photographic element that has increased acutance.

It is thought that the presence of the two types of releasing groups in the described sequence may aid formation of an image having the desired properties. Similar LINK moieties which do not contain the combination of groups as described also do not provide the required increased acutance, as shown by the comparative data in the examples C-1 and C-2 in Table I following. Examples of LINK—Q groups of the invention are represented by the following:

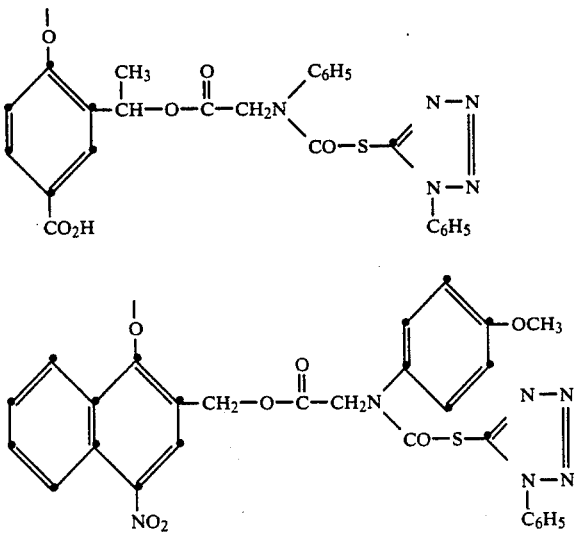

-continued
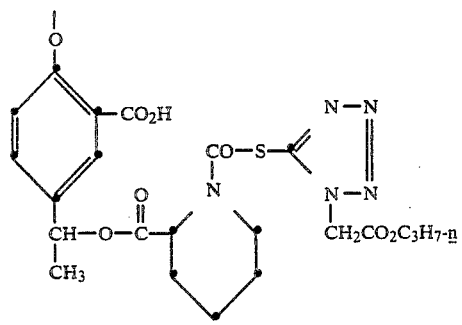
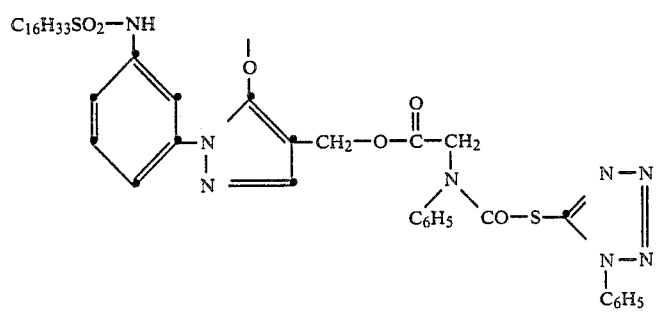
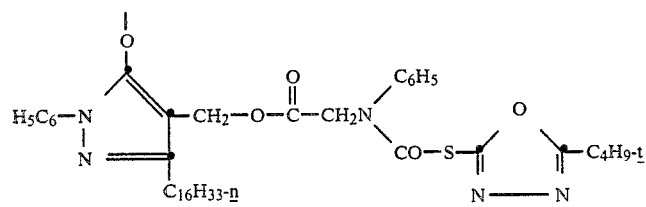
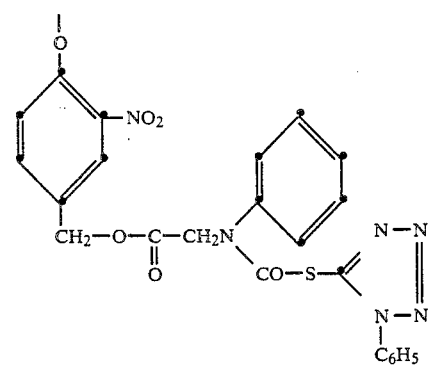
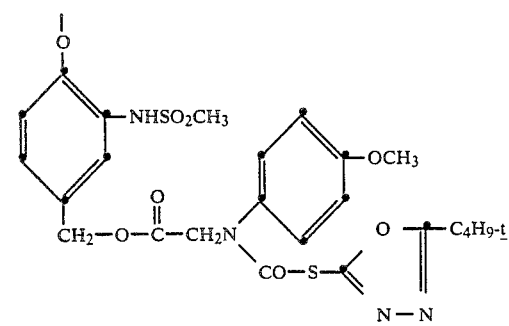

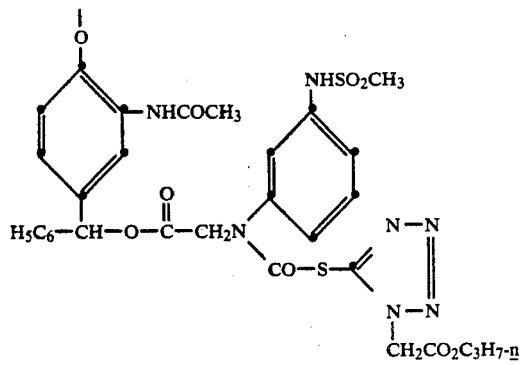

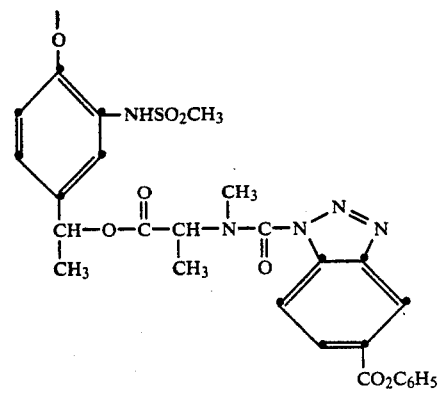

A preferred compound (A) is a dye-forming coupler of the form COUP—LINK—Q in which COUP is a coupler moiety, such as a cyan, magenta or yellow dye-forming coupler moiety, and LINK—Q is a coupling-off group.

A process of forming an image having the described increased acutance comprises developing an exposed photographic silver halide element by means of a color developing agent in the presence of described compound (A), particularly a coupler as described.

Illustrative preferred LINK—Q groups are represented by the formulas:

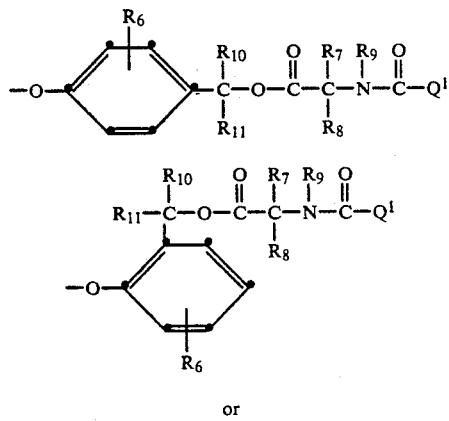

or

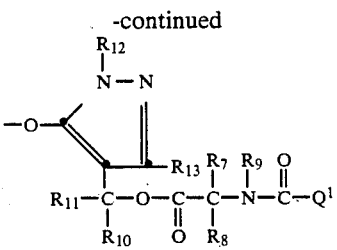

wherein $R_{10}$ and $R_{11}$ individually are hydrogen, unsubstituted or substituted alkyl or aryl or $R_{10}$ and $R_{11}$ together complete a ring system;

$R_6$ is hydrogen, nitro ($-NO_2$), unsubstituted or substituted sulfonamido ($-NHSO_2R$), substituted or unsubstituted sulfamyl ($-SO_2NHR$), substituted or unsubstituted carbonamido ($-NHCOR$), substituted or unsubstituted carbamyl ($-CONHR$) or $-COOR_{13}$ wherein $R_{13}$ is hydrogen, unsubstituted or substituted alkyl or aryl; halogen; or acyl;

$R_{12}$ and $R_{13}$ individually are hydrogen or unsubstituted alkyl or aryl groups;

$R_7$ and $R_8$ individually are hydrogen, unsubstituted or substituted alkyl, such as alkyl containing 1 to 8 carbon atoms, for example, methyl or ethyl; cycloalkyl, such as cyclohexyl and cyclopentyl; or unsubstituted or substituted aryl, such as aryl containing 6 to 10 carbon atoms, such as phenyl or methylphenyl or chlorophenyl, or $R_7$ and $R_8$ together can complete a ring system, such as a 5-, 6- or 7-member ring;

$R_9$ is hydrogen, unsubstituted or substituted alkyl, cycloalkyl, heterocyclic, or aryl; and, $Q^1$ is a releasable development inhibitor group.

The reaction of compound (A), preferably a development inhibitor releasing (DIR) coupler, with oxidized color developing agent cleaves the bond between the coupling-off group (LINK—Q) and the carrier portion of the compound (A), preferably the coupler moiety (COUP). The bond between the first part of the LINK group and the second part of the LINK group is cleaved. The cleavage of the bond between the Q and the second part of LINK is aided by an intramolecular nucleophilic displacement reaction. Tailoring of the structure of the parts of the LINK to requirements of the particular Q group allows control of the desired characteristics of the resulting image in the photographic material. The LINK involves a sequential cleavage of the bond between the first part of the LINK and the second part of the LINK as well as the bond between the LINK and Q.

Particularly useful compounds as described are couplers represented by the formula:

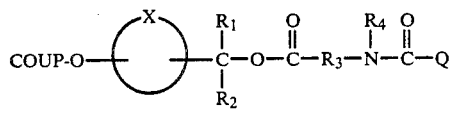

wherein

COUP is a coupler moiety, such as a cyan, magenta or yellow dye forming coupler moiety, X represents the atoms necessary to complete an unsubstituted or substituted arylene or heterocyclic group, as described;

$R_1$ and $R_2$ individually are hydrogen or alkyl;

$R_3$ is a divalent group that enables formation of a ring, such as a 5-, 6- or 7-member ring, upon processing of the photographic element, particularly by mean of an intramolecular nucleophilic displacement reaction;

$R_4$ is hydrogen, unsubstituted or substituted alkyl, cycloalkyl, heterocyclic, or aryl; and, Q is a releasable development inhibitor group.

$R_4$ as described herein is preferably an electron density controlling group that includes an electron withdrawing group or an electron donating group. Examples of useful electron withdrawing groups for $R_4$ include:

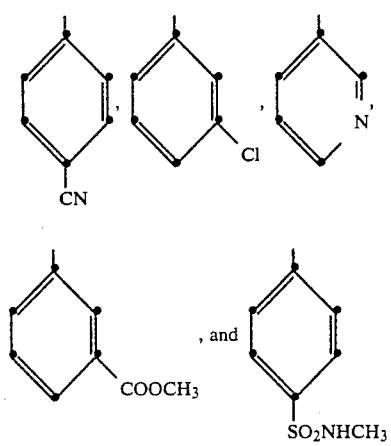

Examples of useful electron donating groups as described for $R_4$ include:

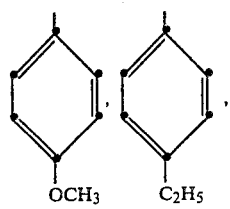

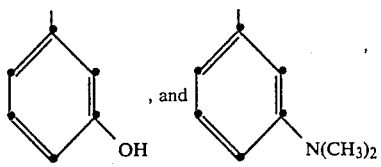

If Q is a mercaptotetrazole group, then $R_4$ typically is an unsubstituted or substituted aryl group as described.

The coupler moiety (COUP) can be any moiety that will react with oxidized color developing agent to cleave the bond between the COUP and the LINK—Q. The coupler moiety includes coupler moieties that have been in conventional color forming couplers in the photographic art to yield colorless products upon reaction with oxidized color developing agents or yield color products on reaction with oxidized color developing agents.

The coupler moiety can be ballasted or unballasted. It can be monomeric, or it can be a dimeric, oligomeric or polymeric coupler, in which case it will contain more than one Q group.

The coupling off group (LINK—Q) is joined to the coupler moiety at a coupling position of the coupler moiety. The coupling off group is released from the coupling position by oxidative coupling reactions known in the photographic art.

As used herein, the term "intramolecular nucleophilic displacement reaction" means a reaction in which a nucleophilic center of a compound reacts directly, or indirectly through an intervening molecule, at another site on the compound, that is an electrophilic center, to effect displacement of a group or atom attached to the electrophilic center. Such compounds have a nucleophilic group and electrophilic group spacially related by the configuration of the molecule to promote reactive proximity. The electrophilic group and the nucleophilic group are located in the coupling-off group as described so that a cyclic organic ring, or a transient cyclic organic ring can be easily formed by an intramolecular reaction involving the nucleophilic center and the electrophilic center.

A nucleophilic group is understood to be a grouping of atoms one of which is electron rich. This atom is referred to as the nucleophilic center. An electrophilic group is understood to be a grouping of atoms one of which is electron deficient. This is referred to as the electrophilic center.

The group Q can be any releasable development inhibitor group known to be useful in the photographic art. The group Q can be present as a preformed species or it can be present as a blocked form or as a precursor. Particularly the Q group can be a preformed development inhibiting group or the development inhibitor can be blocked.

Preferred compound (A) is a photographic coupler containing a ballasted coupler moiety and a Q group that contains sulfur or nitrogen atom bonded to the carbonyl group closest to the Q group in LINK—Q.

A listing of patents follows that describes representative COUP groups useful in the invention. The coupling-off group in each case can be LINK—Q as described.

I. COUP'S

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturübersicht," published in Agfa Mitteilungen, Band III, pp. 156–175 (1961).

Preferably such couplers are phenols and naphthols which form cyan dyes on reaction with oxidized color developing agent B. Couplers which form magenta dyes upon reaction with oxidized color developing agent are described in such representative patents and Publications as: U.S. Pat. Nos. 2,600,788; 2,369,489; 2,343,703; 2,311,082; 3,152,896; 3,519,429; 3,062,653; 2,908,573 and "Farbkuppler-eine Literaturübersicht," published in Agfa Mitteilungen, Band III, pp. 126–156 (1961).

Preferably, such couplers are pyrazolones and pyrazolotriazoles which form magenta dyes upon reaction with oxidized color developing agents and have the LINK—Q attached to the coupling position.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Literaturübersicht," published in Agfa Mitteilungen, Band III, pp. 112–126 (1961).

Preferably such yellow dye forming couplers are acylacetamides, such as benzoylacetanilides and pivaloylacetanilides, and have the LINK—Q group attached to the coupling position, that is the active methylene carbon atom.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959. Preferably such couplers are cyclic carbonyl containing compounds which form colorless products on reaction with oxidized color developing agent.

Illustrative releasable development inhibitor groups (Q) are described in such representative patents as U.S. Pat. Nos. 3,227,554; 3,615,506; 3,617,291; 3,733,201 and U.K. Pat. No. 1,450,479. Preferred development inhibitors are iodide and heterocyclic compounds such as mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, oxadiazoles, benzotriazoles and benzodiazoles. Structures of preferred development inhibitor moieties are:

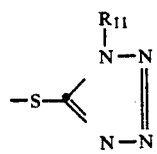

IIIA-1

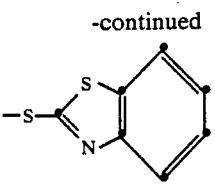

IIIA-2

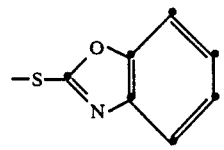

IIIA-3

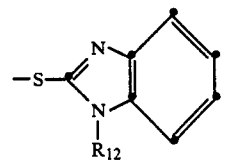

IIIA-4

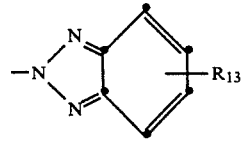

IIIA-5

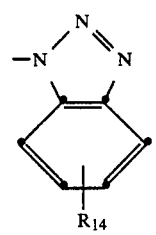

IIIA-6

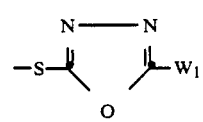

IIIA-7 where $W_1$ is unsubstituted or substituted alkyl, such as butyl, 1-ethylpentyl, and 2-ethoxyethyl, or alkylthio, such as butylthio and octylthio; $R_{11}$ and $R_{12}$ are individually hydrogen, alkyl of 1 to 8 carbon atoms such as methyl, ethyl, or butyl, phenyl or substituted phenyl; and $R_{13}$ and $R_{14}$ are individually hydrogen or one or more halogen such as chloro, fluoro or bromo; alkyl of 1 to 4 carbon atoms, carboxyl, esters such as —COOCH$_3$, or other substituents such as —NHCOOCH$_3$, —SO$_2$OCH$_3$, —OCH$_2$CH$_2$SO$_2$CH$_3$,

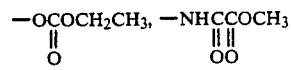

or nitro groups.

The photographic couplers of this invention can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye-image providing material, at least one of the silver halide emulsion units having associated therewith a photographic coupler of the invention. Each silver halide emulsion unit can be composed of one or more layers and the various units and layers can be arranged in different locations with respect to one another.

The couplers of this invention can be incorporated in or associated with one or more layers or units of the photographic element. For example, a layer or unit affected by PUG can be controlled by incorporating in appropriate locations in the element a scavenger layer which will confine the action of PUG to the desired layer or unit. At least one of the layers of the photographic element can be, for example, a mordant layer or a barrier layer.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin polymer, particularly a polymer of an α-olefin containing 2 to 10 carbon atoms such as polyethylene, polypropylene, ethylene-butene copolymers and the like.

The compound (A), particularly photographic couplers, as described, can be used in photographic elements in the same way as photographic couplers that release development inhibitor groups have previously been used in the photographic art. The compound (A) as described can be contained in, or in reactive association with, one or more of the silver halide emulsion units in a color photographic element. If the silver halide emulsion unit is composed of more than one layer, one or more of such layers can contain one or more of the compound (A), particularly the coupler (COUP—LINK—Q) as described.

In the following discussion of suitable materials for use in the emulsions and elements of this invention, reference will be made to *Research Disclosure*, December 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p phenylene diamines. Especially preferred are 4-amino-N,N-diethylaniline hydrochloride; 4-amino-3-methyl-N,N-diethylaniline hydrochloride; 4-amino-3-methyl-N-ethyl-N-β-(methanesulfonamido)ethylaniline sulfate hydrate; 4-amino-3-methyl-N-ethyl-N-β-hydroxyethylaniline sulfate; 4-amino-3-β-(methanesulfonamido)ethyl-N,N-diethylaniline hydrochloride; and 4-amino-N-ethyl-N-(2-methoxyethyl)-m-toluidine di-p-toluenesulfonic acid.

With negative working silver halide the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

The compounds as described can be prepared by reactions and methods known in the organic compound synthesis art. Typically, the couplers are prepared by first attaching the LINK group to the coupling position of the coupler moiety without the Q group present. Then the product is reacted with an appropriate derivative of the Q group to form the desired coupler. Alternatively the Q group may be attached first to the LINK group and then the LINK—Q group is attached to the coupler moiety at the coupling position. The following synthesis illustrates the methods of preparation:

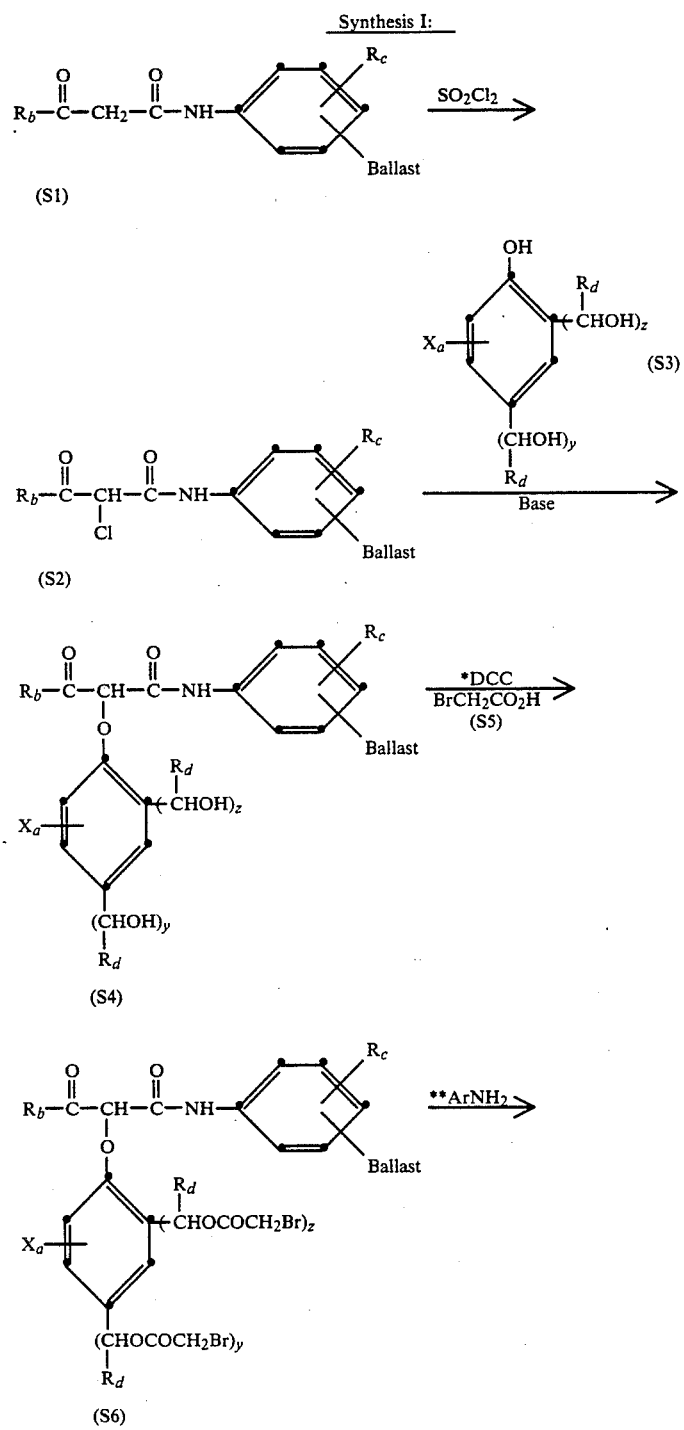

-continued

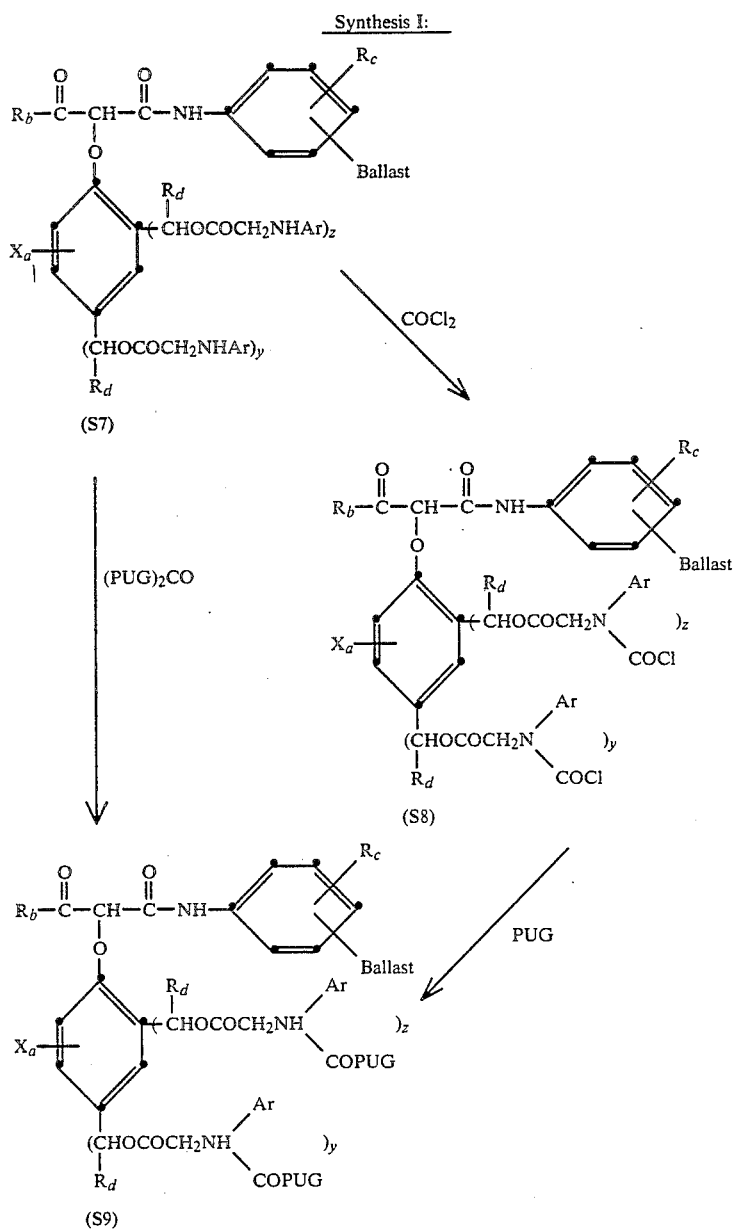

y and z above are each 0 or 1 and one of y and z is 0.
*DCC herein means dicyclohexylcarbodiimide.
**Ar herein means aryl, preferably phenyl.

In the above compounds $R_b$ is alkyl or aryl, such as t-butyl or p-methoxyphenyl; $R_c$ is a substituent, such as chlorine or alkoxy, such as methoxy; ballast is a ballast group as described; $X_a$ is hydrogen or a substituent that does not adversely affect the coupler, such as sulfonamido or carbonamido; $R_d$ is hydrogen or unsubstituted or substituted alkyl, such as methyl.

In the described process the coupler S1 is reacted with sulfonyl chloride to form S2 containing chlorine in the coupling position. The resulting S2 is reacted with phenolic compound S3 in the presence of base to form compound S4. Compound S4 is reacted with S5 and DCC to form S6. Compound S6 is reacted with ArNH₂, typically aniline, to form S7. Compound S7 can be used to form desired coupler S9 by alternative routes using (PUG)₂CO or using COCl₂ to form S8 and then reaction with PUG.

The following examples illustrate preparation of compounds of the invention:

SYNTHESIS EXAMPLE A

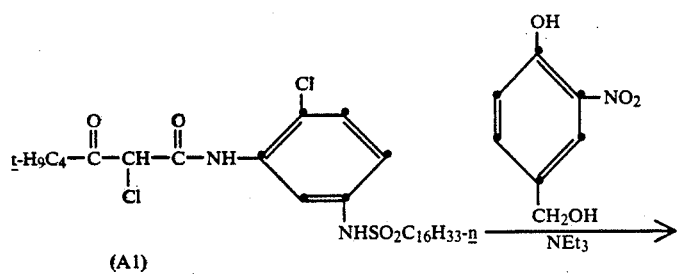
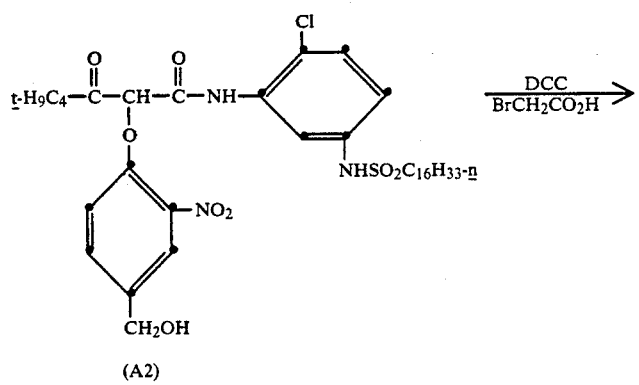
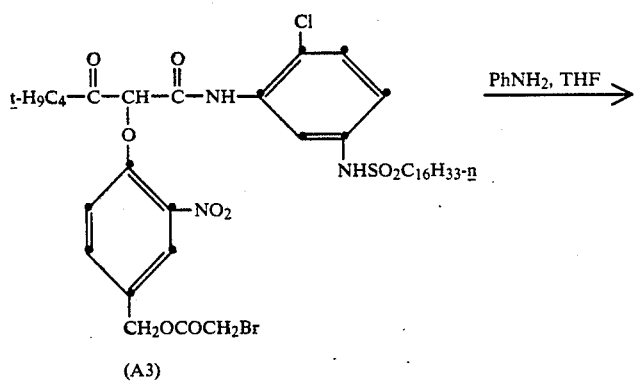
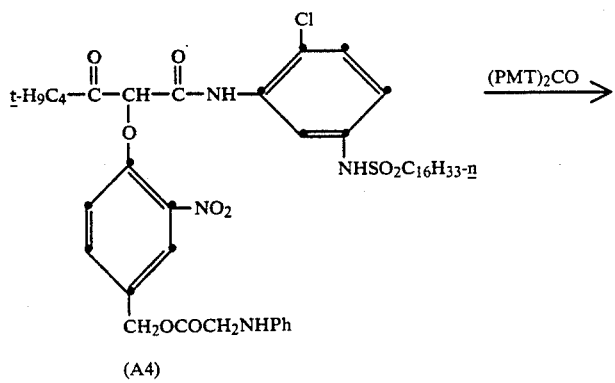

-continued

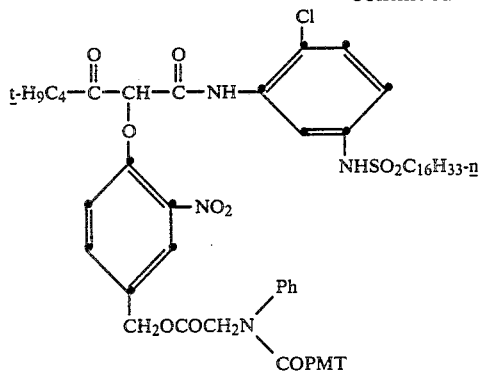

(A5)

Ph herein means phenyl.
PMT herein means phenylmercaptotetrazole.
Et herein means ethyl.
(PMT)₂CO herein means bis-phenylmercaptotetrazole carbonyl, also described as bis-PMT-carbonyl.

Compound (A2)

Chloroketoamide (A1), (10.0 g, 16.9 mmol) was dissolved in dimethylformamide (100 mL). To this solution was then added 4-hydroxymethyl 2-nitrophenol (2.86 g, 16.9 mmol), followed by triethylamine (7.05 mL, 50.7 mmol) and the reaction mixture stirred under nitrogen at room temperature for 5 hours. The reaction solution was then poured into 2N—HCl and extracted with ethyl acetate (X3). The combined ethyl acetate extracts were then washed with 2N—HCl (X3), dried (MgSO₄), filtered and concentrated to an oil under reduced pressure. The oil was then dissolved in 40% ethyl acetate in heptane and subjected to flash chromatography eluting with the same solvent system. The major band was collected to give the product, compound (A2), 7.5 g (61%).

Compound (A3)

Compound (A2), (7.5 g, 10.4 mmol) was dissolved in ethyl acetate (60 mL). To this solution was added dicyclohexylcarbodiimide (2.37 g, 11.49 mmol), bromoacetic acid (2.39 g, 17.2 mmol) and a catalytic amount of N,N-4-dimethylaminopyridine (100 mg). The resulting reaction solution was then stirred at room temperature for 30 minutes after which time a TLC (40% ethyl acetate in heptane) showed complete reaction. The precipitated dicyclohexylurea was then filtered off, washed with a little ethyl acetate and the filtrate concentrated under reduced pressure. The product so obtained, compound (A3), was pure enough to be taken on directly to the next step. Yield 100%.

Compound (A4)

Compound (A3), (10.4 mmol) was dissolved in tetrahydrofuran (60 mL). To this solution was then added aniline (9.7 mL, 106.0 mmol) and the resulting solution stirred at room temperature for approximately 18 hours. The solvent was removed under reduced pressure, the residue taken up in ethyl acetate, washed with 2H—HCl (X3), dried MgSO₄), filtered and concentrated under reduced pressure. This product was sufficiently pure to be used as such in the next step. Yield 100%.

Compound (A5)

Compound (A4), (5.75 g, 6.6 mmol) was taken up in tetrahydrofuran (60 mL) and to this solution was added bis-PMT-carbonyl (3.33 g, 8.71 mmol). The reaction was then stirred at room temperature for 2 hours. At the end of this period a further batch of the bis-PMT-carbonyl (1.28 g, total 4.61 g, 12.04 mmol) was then added and the reaction solution stirred for 12 hours. The solvent was removed under reduced pressure and the residue taken up in ethyl acetate. The ethyl acetate was then washed with 2.5% $Na_2CO_3$ (X3) followed by 2H—HCl (X1), dried (MgSO₄), filtered and concentrated. The residue was then taken up in 50% ethyl acetate in heptane and subjected to flash chromatography eluting with the same solvent mixture. The first major band was collected to give the product, compound (A5), 3.5 g (50%).

Calculated for $C_{52}H_{65}ClN_8O_{10}S_2H_2O$:
%C=57.85, %H=6.25, %N=10.38, %S=5,94, %Cl=13.28
Found: %C=57.9, %H=5.9, %N=11.3, %S=5.8, %Cl=12.9.

SYNTHESIS EXAMPLE B

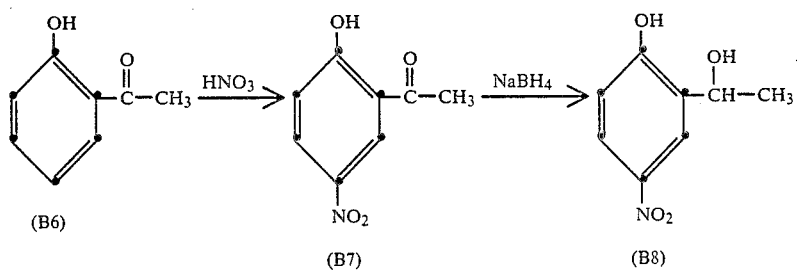

-continued
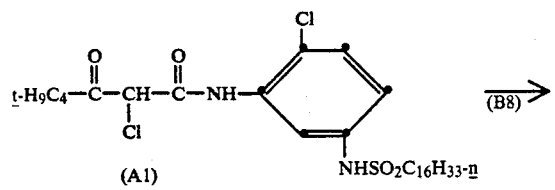
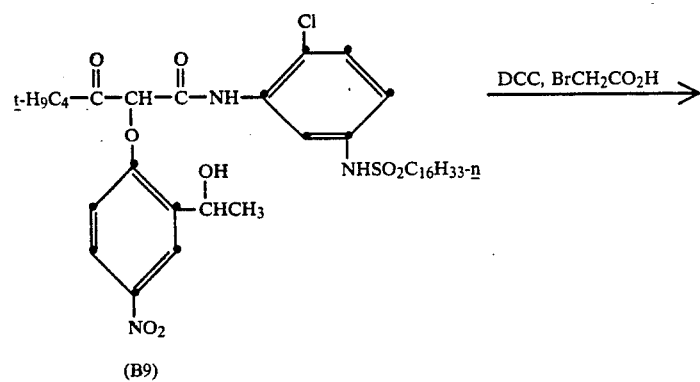
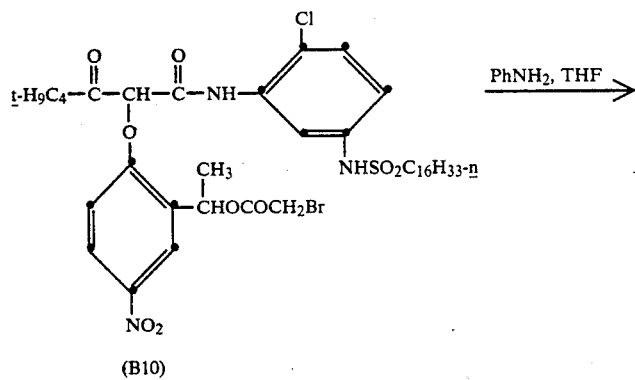
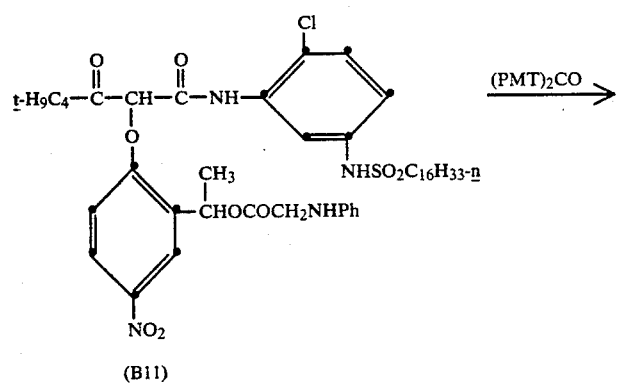

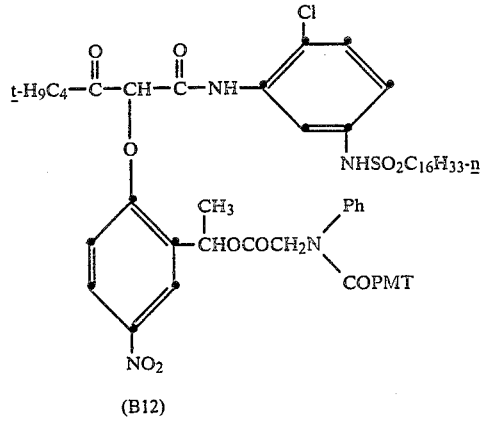

(B12)

2-Hydroxy-5-nitroacetophenone, (B7)

2-Hydroxyacetophenone (25.0 g, 183.62 mmol) (B6) was taken up in acetic acid (150 mL) and heated to 35° C. To this solution was then added concentrated nitric acid (26 mL) dropwise over 1.5 hours. After the addition the reaction mixture was stirred overnight at room temperature and worked up by pouring into ice water. The oil so obtained was extracted with ethyl acetate. The ethyl acetate layer was then dried (MgSO$_4$), filtered, concentrated to an oil under reduced pressure and coevaporated with heptane to remove residual acetic acid. The residue was taken up in 50% dichloromethane in heptane and subjected to flash chromatography eluting with the same solvent mixture. The first major band was collected and concentrated to give the desired 2-hydroxy-5-nitroacetophenone, yield 12.0 g (39%). The 2-hydroxy-3-nitroacetophenone isomer was also formed in this reaction and could readily be isolated from the same chromatography column.

2-(1-Hydroxyethyl)-4-nitrophenol, (B8)

The acetophenone (120 g, 66.24 mmol) was suspended in methanol (40 mL) and water (160 mL) added. Sodium borohydride (2.5 g, 66.24 mmol) was then added portionwise over a 15 minute period. The solution went yellow and foamed during the addition of the sodium borohydride. The resulting suspension was stirred at room temperature for 15 minutes and then made acidic with the addition of 2H—HCl to give a clear solution. The 2-(1-hydroxymethyl)-4-nitrophenol was isolated from the reaction solution by salting out. The product was then filtered off, washed with a little cold water and air dried. Yield 11.8 g (97%).

Compound (B9)

The chloroketoamide (A1) (16.15 g, 27.30 mmol) together with 2-(1-hydroxyethyl)-4-nitrophenol (B8) (5.0 g, 27.30 mmol) were taken up in dry dimethylformamide (150 mL). Triethylamine (15 mL, 109.20 mmol) was then added and the resulting solution stirred at room temperature for 8 hours. The reaction was then diluted with ethyl acetate and washed with 2H—HCl (X3). The organic layer was then dried (MgSO$_4$), filtered and taken to an oil under reduced pressure. The oil was dissolved in a solvent mixture containing dichloromethane, ethyl acetate and heptane in the ratio of 5:10:35, respectively, (100 mL) and flash chromatographed over silica gel eluting with the same solvent mixture. The first major band was collected to give compound (B9), 15.5 g (77%).

Compound (B10)

Compound (B9) (15.5 g, 21.0 mmol) was dissolved in dichloromethane, (100 mL). To this solution was then added dicyclohexylcarbodiimide (4.76 g, 23.1 mmol), bromoacetic acid (3.21 g, 23.1 mmol) and a catalytic amount of N,N-4-dimethyl-aminopyridine (100 mg). While stirring at room temperature and over a 15-minute period the dicyclohexylurea by product precipitated out of the reaction mixture. The urea was filtered off, washed with a little dichloromethane and the combined filtrate taken to an oil under reduced pressure. The residual oil, compound (B10), was pure enough to be used directly, without further purification, in the next step. Yield 100%.

Compound (B11)

Compound (B10) (21.0 mmol) was dissolved in tetrahydrofuran (200 mL), and aniline (19.5 mL, 210.0 mmol) was added. The resulting solution was then stirred at room temperature for 18 hours. At the end of this period the reaction solution was concentrated to an oil under reduced pressure, taken up in ethyl acetate, which was washed with 2N—HCl (X3), dried (MgSO$_4$). filtered and concentrated to an oil again. This gave the product, compound (B11), pure enough to be carried on to the next stage of the reaction. Yield 100%.

Compound (B12)

Compound (B11) (21.0 mmol) together with bis-PMT-carbonyl (8.0 g, 21.0 mmol) were dissolved in tetrahydrofuran (150 mL) and stirred at room temperature for 1 hour. The solvent was removed under reduced pressure and the oil taken up in ethyl acetate. The ethyl acetate solution was then washed with 2.5% Na$_2$CO$_3$ (X3), 2N—HCl (X1), dried (MgSO$_4$), filtered and the ethyl acetate removed under reduced pressure. The residual oil was taken up in a solvent mixture containing dichloromethane, ethyl acetate and heptane in the ratio of 10:25:65, respectively, and subjected to flash chromatography. The major band was collected and concentrated to give the product, compound (B12), yield 11.0 g (49% calculated from compound (B9)).

Calculated for C$_{53}$H$_{67}$ClN$_8$O$_{10}$S$_2$
%C=59.2, %H=6.3, %N=10.4, %Cl=13.3, %S=6.0
Found: %C=59.3, %H=6.1, %N=10.6, %Cl—13.1, %S=6.4.

SYNTHESIS EXAMPLE C

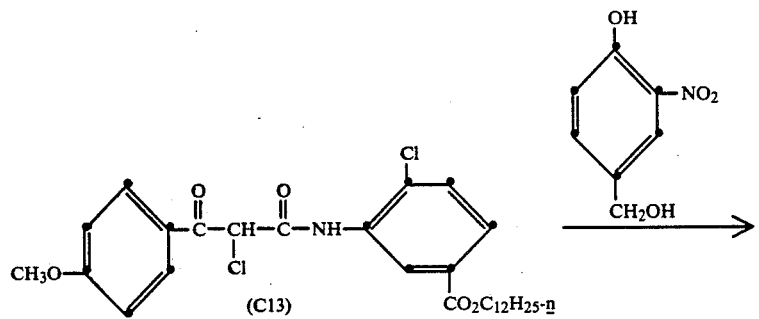
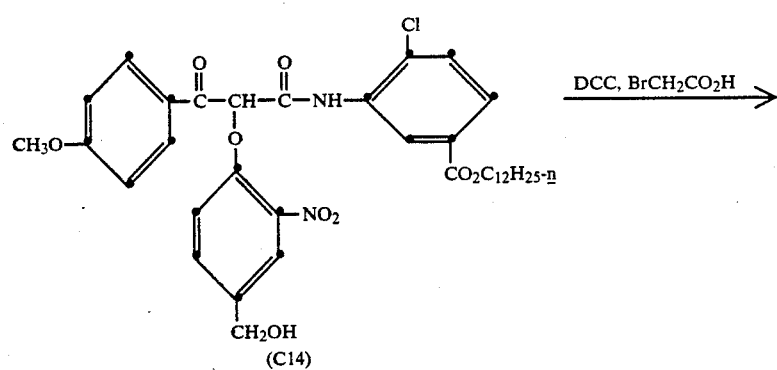
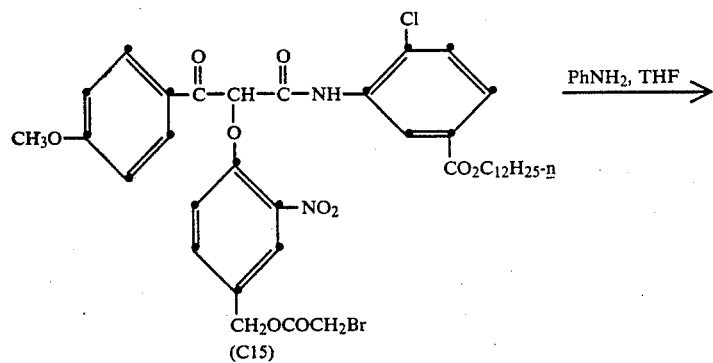
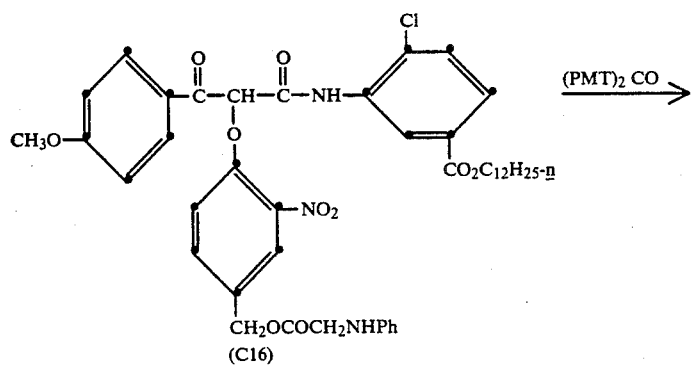

-continued

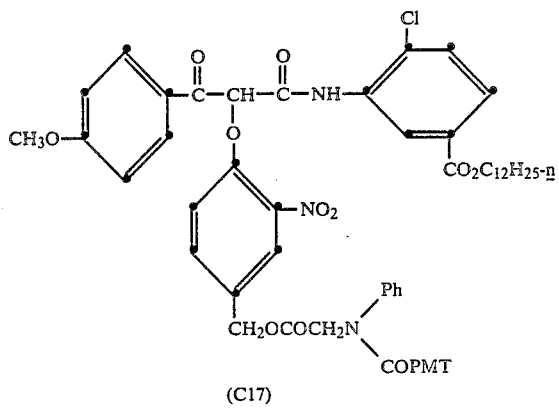

(C17)

Compound (C14)

The chloroketoamide (C13), (10.0 g, 18.17 mmol) was taken up in dimethylformamide (100 mL). To this solution was then added 4-hydroxymethyl-2-nitrophenol (3.07 g, 18.17 mmol), followed by triethylamine (12.6 mL, 90.85 mmol) and the resulting solution stirred at room temperature for 8 hours. At the end of this period the reaction was worked up by pouring into 2H—HCl and extracting with ethyl acetate (X3). The combined ethyl acetate extracts were then washed with 2N—HCl (X3), dried (MgSO$_4$), filtered and taken to an oil. The oil was taken up in 20% ethyl acetate in dichloromethane and flash chromatographed eluting with the same solvent system. The first major band was collected and the solvent removed under reduced pressure to give compound (C14), 5.9 g (48%).

Compound (C15)

Compound (C14), (5.9 g, 8.6 mmol) was taken up in ethyl acetate (60 mL). To this solution was added dicyclohexylcarbodiimide (1.78 g, 8 6 mmol), bromoacetic acid (1.79 g, 12.9 mmol) and a catalytic amount of N,N-4-dimethylaminopyridine (100 mg). The reaction was complete in 30 minutes as shown by a TLC (silica gel, 40% ethyl acetate in heptane). The dicyclohexylurea by-product was then filtered off and washed with a little ethyl acetate. The filtrate was concentrated to an oil under reduced pressure, taken up in 30% ethyl acetate in heptane and subjected to flash chromatography eluting with the same solvent system. The first major band was collected and the solvent removed under reduced pressure to give compound (C15), 4.0 g (58%).

Compound (C16)

Compound (C15) (4.0 g, 4.97 mmol) was taken up in tetrahydrofuran (40 mL), aniline (4.5 mL, 49.7 mmol) added and the reaction mixture stirred at room temperature for 18 hours. At the end of this period the reaction was heated to 50° C. and held at this temperature for 4 hours. A TLC (silica gel, 50% ethyl acetate in heptane) showed no starting material. The reaction was poured into ice cold 2N—HCl and extracted with ethyl acetate (X3). The ethyl acetate extracts were combined, dried (MgSO$_4$), filtered and concentrated to an oil. The oil was taken up in 30% ethyl acetate in heptane and subjected to flash chromatography to give compound (C16), yield 1.6 g (39%).

Compound (C17)

Compound (C16), (1.6 g, 1.96 mmol) was dissolved in tetrahydrofuran (20 mL). To this solution was then added the bis-PMT-carbonyl (1.35 g, 3.53 mmol) and the reaction mixture was stirred at room temperature for 18 hours. The solvent was then removed under reduced pressure, the residual oil taken up in ethyl acetate and washed first with 2.5% Na$_2$CO$_3$ (X3) and then with 2H—HCl (X1) and finally dried (MgSO$_4$). After filtering the ethyl acetate was removed under reduced pressure, the residue taken up in 35% ethyl acetate in heptane and flash chromatographed over silica gel eluting with the same solvent system. The first major band gave the product, compound (C17), 1.2 g (60%).

Calculated for $C_{52}H_{54}ClN_7O_{11}S$:

%C=61.2, %H=5.3, %N=9.5, %Cl=13.5, %S=3.1

Found: %C=60.9, %H=5.1, %N=9.5, %Cl=13.6, %S=3.0.

Another illustrative method of synthesis is as follows:

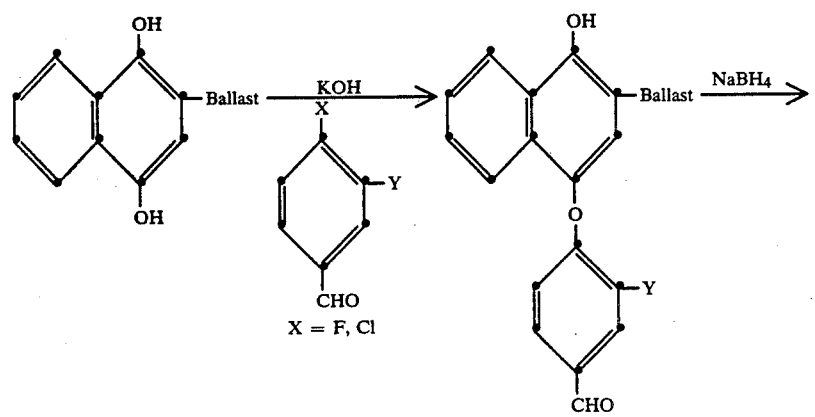
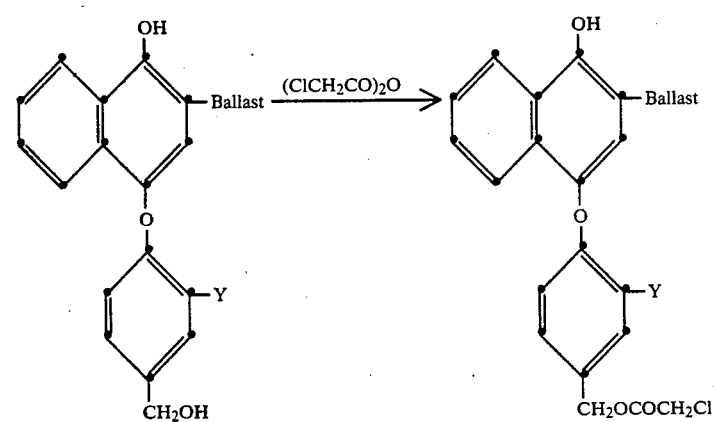
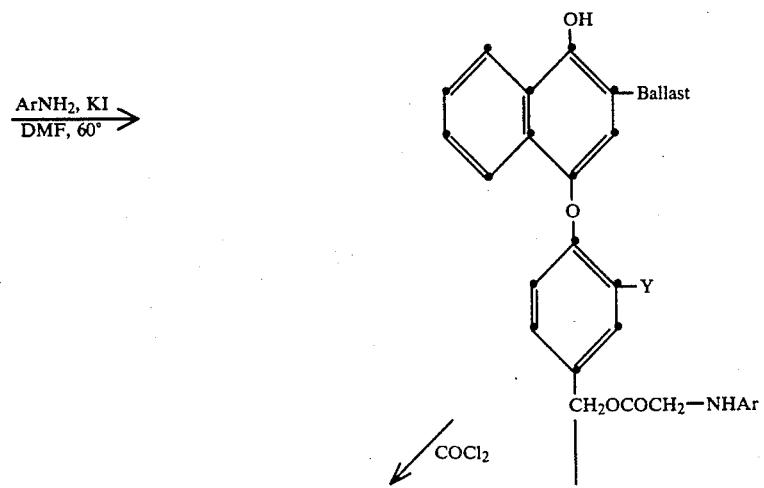

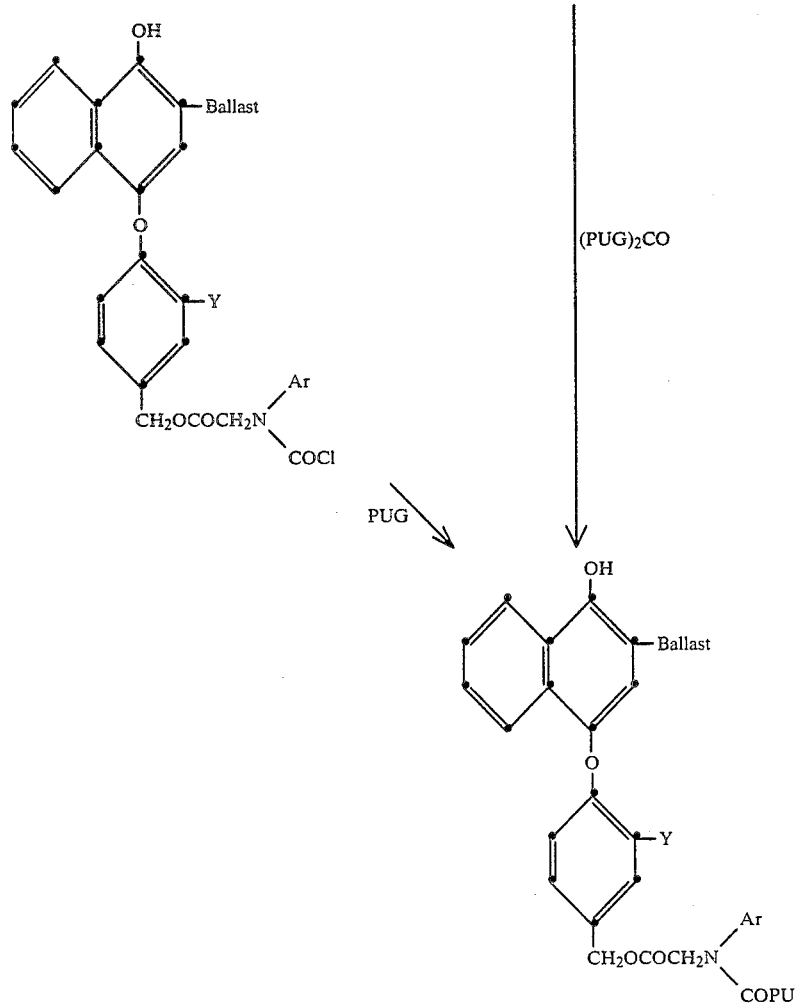
SYNTHESIS EXAMPLE D
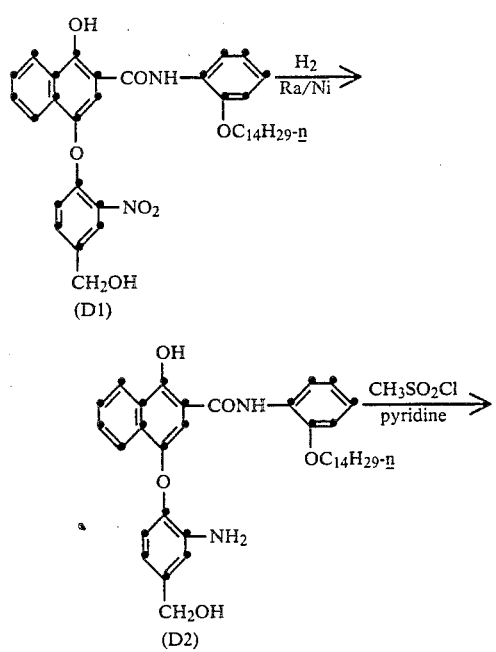
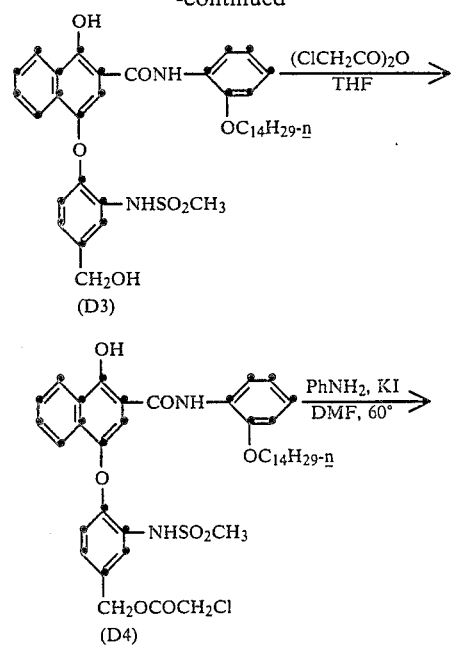

-continued

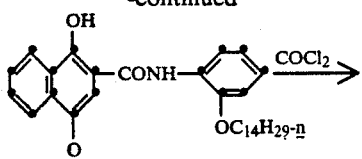

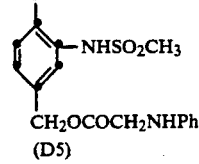

CH₂OCOCH₂NHPh (D5)

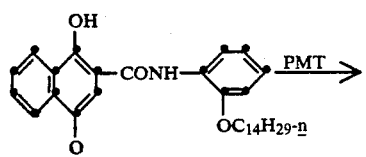

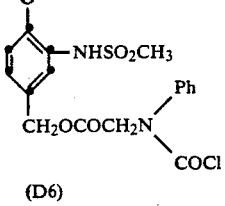

(D6)

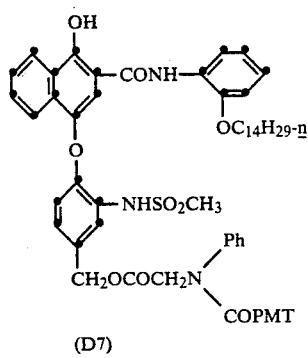

(D7)

Compound (D2)

The nitrobenzyl alcohol (D1) (10.0 g, 15.56 mmol) was dissolved in tetrahydrofuran (50 mL) and methanol (100 mL) added. Some Raney-Nickel which had been washed with water, then methanol, several times was then added and the mixture hydrogenated at 55 psi at room temperature. Hydrogen up-take was complete in 1 hour. The catalyst was filtered off, carefully washed with a little tetrahydrofuran and the solvent removed from the filtrate under reduced pressure. The hydrogenation was clean, it was assumed to give 100% yield and used directly in the next step.

Compound (D3)

Compound (D2) (15.56 mmol) was taken up in dry pyridine (50 mL) and methanesulfonyl chloride (1.21 mL, 15.56 mmol) in dry tetrahydrofuran (20 mL) was added dropwise over a period of 15 minutes. The reaction was stirred at room temperature for 30 minutes. A TLC (silica gel, 30% ethyl acetate in heptane) still showed some starting material. A further batch of methanesulfonyl chloride (0.2 mL) was added and the reaction stirred for an additional 30 minutes. The pyridine was then removed under reduced pressure and the residue taken up in ethyl acetate. The ethyl acetate was then washed with 2N—HCl (X1), dried (MgSO₄), filtered and concentrated under reduced pressure. The residue was taken up in 30% ethyl acetate in heptane and subjected to flash chromatography eluting with the same solvent system. The first major band was collected to give the product, compound (D3), yield 3.0 g (28% from the starting nitro compound (1D)).

Compound (D4)

Compound (D3) (10.23 g, 14.81 mmol) was dissolved in dry tetrahydrofuran (100 mL) to which was added pyridine (1.32 mL, 16.29 mmol). This solution was stirred at room temperature and chloroacetic anhydride (2.8 g, 16.29 mmol) in tetrahydrofuran (20 mL) was then added dropwise with stirring. After stirring at room temperature for 1 hour further batches of pyridine (0.12 mL) and chloroacetic anhydride (0.24 g) were added and stirring continued for another hour. The solvent was then removed under reduced pressure, and the residue taken up in ethyl acetate. The ethyl acetate solution was then washed with 2H—HCl (X1), dried (MgSO₄) and the solvent removed under reduced pressure. The residue crystallized from a solvent mixture of ethyl acetate, dichloromethane and heptane in the ratio of 20:10:70, respectively. Yield 7.3 g (64%).

Compound (D5)

Compound (D4) (7.3 g, 9.52 mmol) was dissolved in dimethylformamide (70 mL) to which was then added potassium iodide (2.37 g, 14.27 mmol) and aniline (3.53 mL, 38.05 mmol). The reaction mixture was then heated at 60° C. for 1 hour. The reaction was then cooled, poured into 2H—HCl, extracted with ethyl acetate (X2), the ethyl acetate extracts combined, washed with 2N—HCl (X3), dried (MgSO₄), filtered and concentrated under reduced pressure. The residue was taken up in 20% ethyl acetate in heptane from which compound (D5) crystallized. Yield 5.7 g (73%).

Compound (D6)

Compound (D5) (5.7 g. 6.92 mmol) was dissolved in tetrahydrofuran (60 mL) to which was then added a solution of phosgene in toluene (17 mL of a 12% solution, 20.75 mmol) followed by N,N-diethylaniline (1.1 mL, 6.92 mmol) while stirring at room temperature. After 15 minutes the solution was concentrated under reduced pressure to give compound (D6), crude. Yield 100%.

Compound (D7)

Compound (D6) (6.92 mmol) as described above, was dissolved in dry pyridine (50 mL) and stirred at room temperature. To the reaction solution was added PMT (1 7 g, 8.30 mmol) and stirred for a period of 1 hour. The reaction solution was concentrated under reduced pressure, taken up in ethyl acetate, washed with 2N—HCl (X3), dried (MgSO₄), filtered and concentrated to an oil. The residue was taken up in a solvent mixture of ethyl acetate, dichloromethane, heptane in the ratio of 20:20:60, respectively, and flash chromatographed eluting with the same solvent system. The first major band was collected. Yield 5.8 g (82%).

Calculated for $C_{55}H_{61}ClN_7O_9S_2$:

%C=64.25, %H=5.98, %N=9.54, %S=6.24

Found: %C=64.37, %H=5.92, %N=9.53, %S=6.43.

Examples of couplers prepared by the described methods include the following:

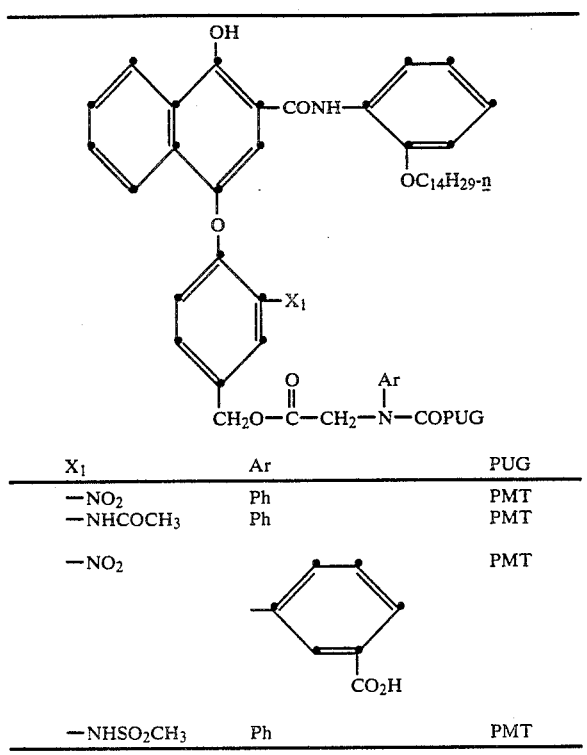

| $X_1$ | Ar | PUG |
|---|---|---|
| —NO$_2$ | Ph | PMT |
| —NHCOCH$_3$ | Ph | PMT |
| —NO$_2$ | (4-CO$_2$H-phenyl) | PMT |
| —NHSO$_2$CH$_3$ | Ph | PMT |

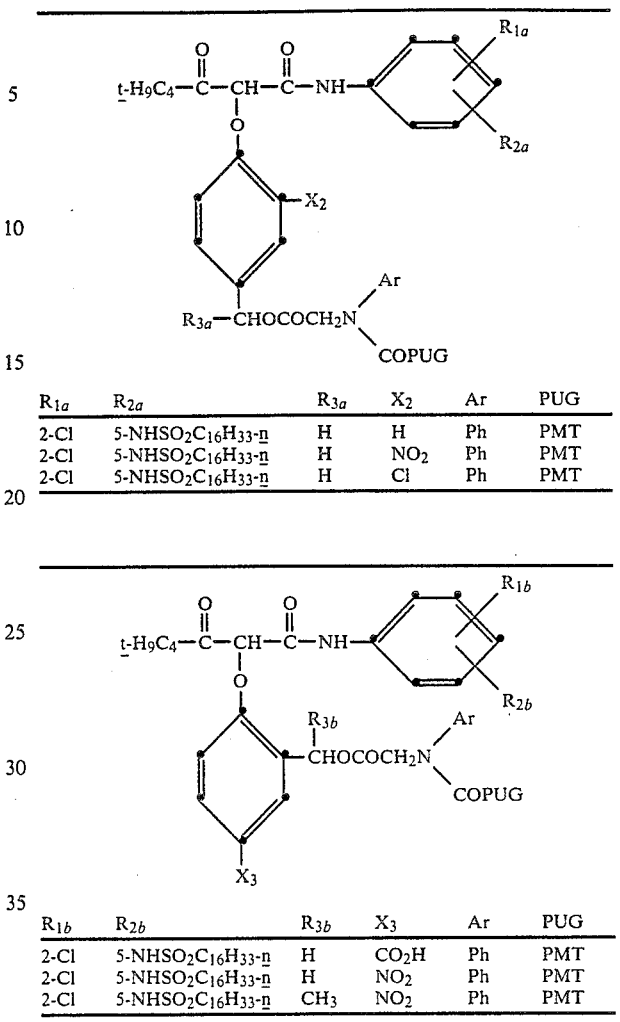

| $R_{1a}$ | $R_{2a}$ | $R_{3a}$ | $X_2$ | Ar | PUG |
|---|---|---|---|---|---|
| 2-Cl | 5-NHSO$_2$C$_{16}$H$_{33}$-n | H | H | Ph | PMT |
| 2-Cl | 5-NHSO$_2$C$_{16}$H$_{33}$-n | H | NO$_2$ | Ph | PMT |
| 2-Cl | 5-NHSO$_2$C$_{16}$H$_{33}$-n | H | Cl | Ph | PMT |

| $R_{1b}$ | $R_{2b}$ | $R_{3b}$ | $X_3$ | Ar | PUG |
|---|---|---|---|---|---|
| 2-Cl | 5-NHSO$_2$C$_{16}$H$_{33}$-n | H | CO$_2$H | Ph | PMT |
| 2-Cl | 5-NHSO$_2$C$_{16}$H$_{33}$-n | H | NO$_2$ | Ph | PMT |
| 2-Cl | 5-NHSO$_2$C$_{16}$H$_{33}$-n | CH$_3$ | NO$_2$ | Ph | PMT |

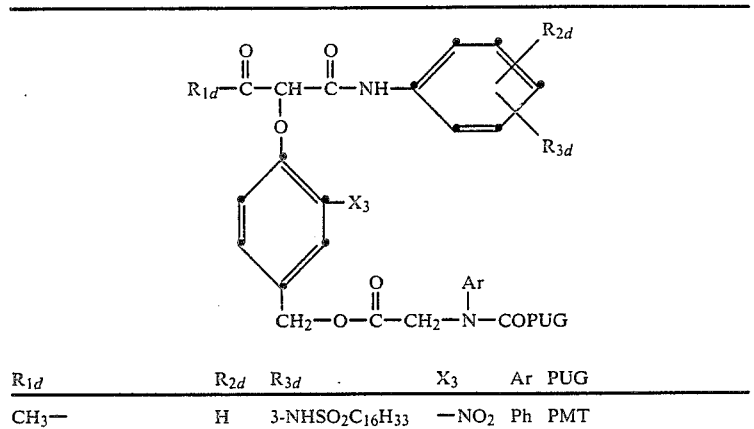

| $R_{1d}$ | $R_{2d}$ | $R_{3d}$ | $X_3$ | Ar | PUG |
|---|---|---|---|---|---|
| CH$_3$— | H | 3-NHSO$_2$C$_{16}$H$_{33}$ | —NO$_2$ | Ph | PMT |
| (4-CH$_3$O-phenyl) | 2-Cl | 5-SO$_2$NHC$_{16}$H$_{33}$ | —NO$_2$ | Ph | PMT |

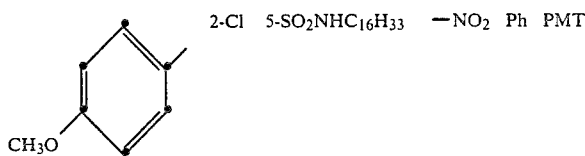

-continued

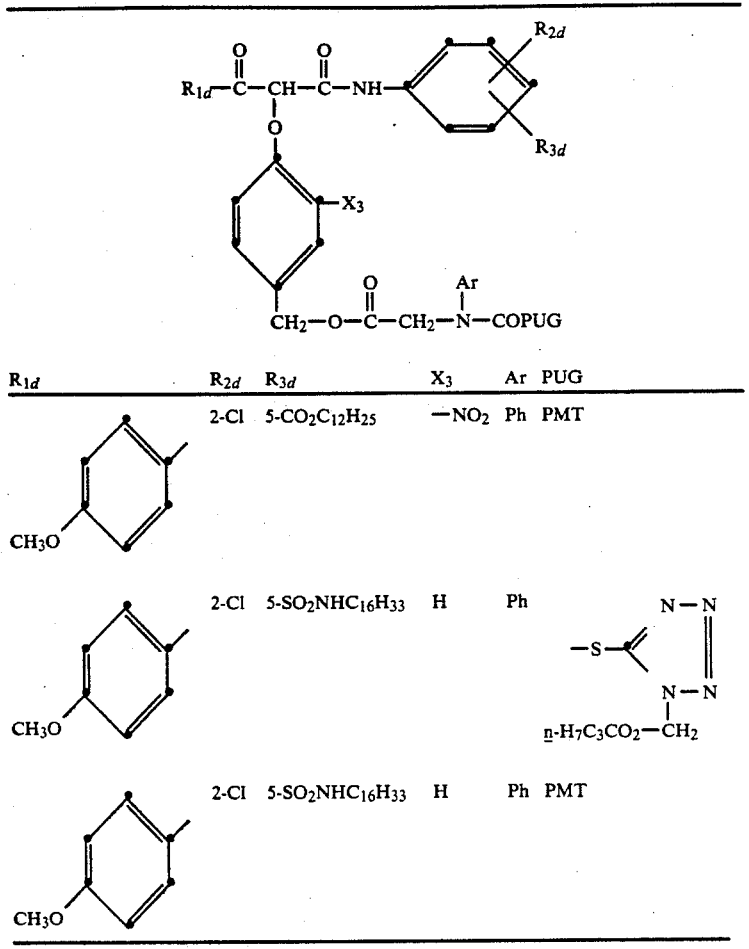

| $R_{1d}$ | $R_{2d}$ | $R_{3d}$ | $X_3$ | Ar | PUG |
|---|---|---|---|---|---|
| ![CH3O-phenyl] | 2-Cl | 5-CO$_2$C$_{12}$H$_{25}$ | —NO$_2$ | Ph | PMT |
| ![CH3O-phenyl] | 2-Cl | 5-SO$_2$NHC$_{16}$H$_{33}$ | H | Ph | (triazole-S group) |
| ![CH3O-phenyl] | 2-Cl | 5-SO$_2$NHC$_{16}$H$_{33}$ | H | Ph | PMT |

The following examples further illustrate the invention.

EXAMPLES 1-11

Photographic elements were prepared by coating the following layers on a cellulose ester film support (amounts of each component are indicated in mg/m$^2$):

| | |
|---|---|
| Emulsion layer 1: | Gelatin -2420; red sensitized silver bromoiodide (as Ag) - 1615; yellow image coupler dispersed in dibutyl phthalate (RECEIVER LAYER) |
| Interlayer: | Gelatin - 860; didodecylhydroquinone - 113 |
| Emulsion layer 2: | Gelatin - 2690; green sensitized silver bromoiodide (as Ag) - 1615; magenta image coupler dispersed in tritolyl phosphate or cyan image coupler dispersed in dibutyl phthalate; DIR compound of Table 1 dispersed in N,N-diethyl-dodecanamide and coated at a level sufficient to provide a contrast of 0.5 (half) of the original contrast after stepwise green light exposure and processing (CAUSER LAYER) |
| Protective Overcoat | Gelatin - 5380; bisvinylsulfonylmethyl ether at 2% total gelatin. |

Structures of the image couplers are as follows:

Cyan Image Coupler (B):

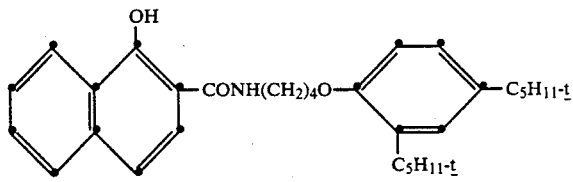

Magenta Image Coupler:

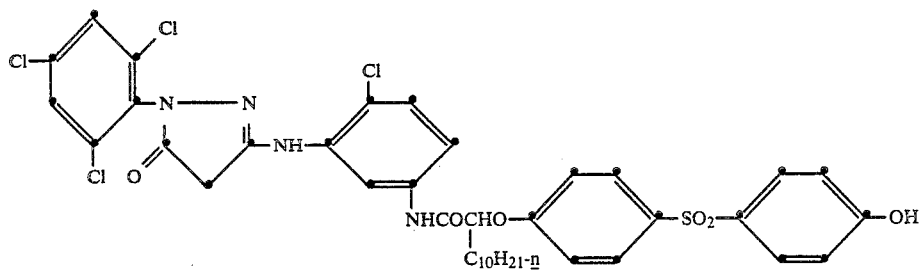

Yellow Image Coupler:

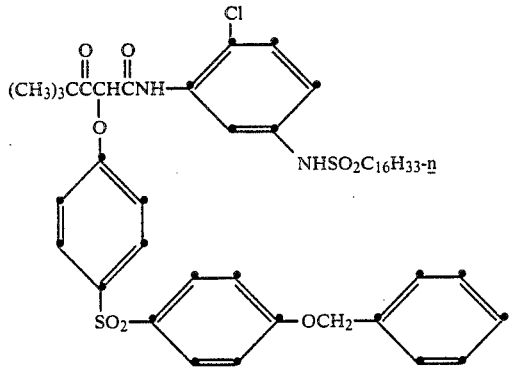

Strips of each element were exposed to green light through a graduated density step tablet, or through a 35% modulation fringe chart for sharpness measurements, and then developed 3.25 minutes at 38° C. in the following color developer, stopped, washed, bleached, fixed, washed and dried.

| Color Developer: | |
| --- | --- |
| Distilled water | 800 mL |
| Sodium Metabisulfite | 2.78 g |
| Sodium Sulfite, anhydrous | 0.38 g |
| CD-4 (color developer)* | 4.52 g |
| Potassium Carbonate, anhyd. | 34.3 g |
| Potassium Bicarbonate | 2.32 g |
| Sodium Bromide | 1.31 g |
| Potassium Iodide | 1.20 mg |
| Hydroxylamine Sulfate (HAS) | 2.41 g |
| Diethylenetriaminepentacetic acid, pentasodium salt (40% Soln.) | 8.43 g |
| Distilled water | to 1 L |
| Adjust pH to 10.0. | |

*CD-4 is 4-amino-3-methyl-N-ethyl-N-beta-hydroxy-ethylaniline sulfate.

Processed images were read with green light to determine the contrast and AMT acutance. From plots of AMT acutance vs. the logarithm of the contrast for variations in the coated level of each development inhibitor releasing (DIR) compound, the acutance was determined at a contrast of 0.5 compared to its original contrast without the presence of the DIR compound. The acutance for a control DIR coupler was subtracted from each AMT value to provide the relative sharpness value reported as the change in AMT in Table I. AMT calculations employed the following formula in which the cascaded area under the system modulation curve is shown in equation (21.104) on page 629 of the "Theory of the Photographic Process", 4th Edition, 1977, edited by T. H. James: $AMT = 100 + 66 Log[cascaded\ area/2.6696M]$ wherein th magnification factor M is 3.8 for the 35 mm system AMT. The use of CMT acutance is described by R. G. Gendron in "An Improved Objective Method of Rating Picture Sharpness: CMT acutance" in the Journal of SMPTE, Vol. 82, pages 1009-12, (1973). AMT is a further modification of CMT useful for evaluating systems which include the viewing of a positive print made from a negative.

Interimage effect (the degree of color correction) was evaluated after a daylight exposure. Interimage, in this case, was quantified as the ratio of the gamma of the green sensitive layer (causer) to that of the red sensitive layer (receiver).

TABLE I

| Example No./ Coupler No. | Change in AMT | Gamma Causer Gamma Receiver |
| --- | --- | --- |
| Cntrl Cplr | 0 | 1.0 |
| *1 | 5.2 | 1.2 |
| *2 | 2.8 | 1.2 |
| 3 | 3.3 | 1.3 |
| 4 | 1.4 | 1.0 |
| *5 | 3.6 | 2.8 |
| 6 | 2.4 | 1.9 |
| 7 | 1.7 | 1.1 |
| 8 | 2.7 | 1.3 |
| 9 | 4.1 | 1.4 |
| 10 | 3.0 | 1.5 |
| 11 | 2.1 | 1.4 |
| *C-1 (Comparison) | 0 | 0.6 |
| *C-2 (Comparison) | 0 | 0.6 |

*Use cyan image coupler B as described.

Control Coupler:

-continued
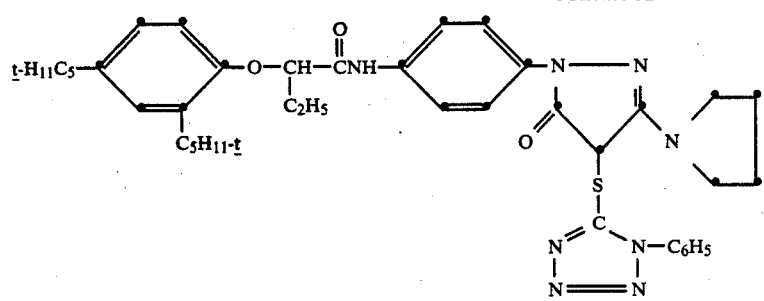
Coupler 1
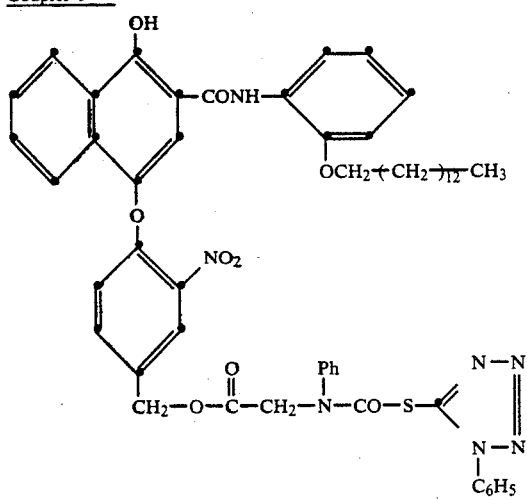
Coupler 2
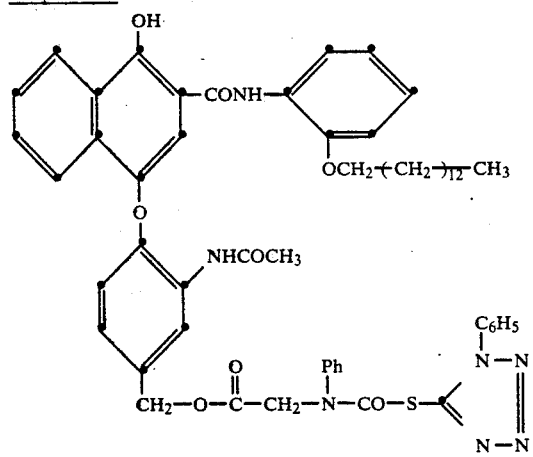
Coupler 3
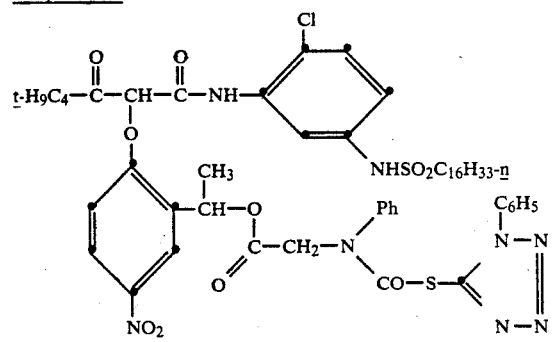
Coupler 4

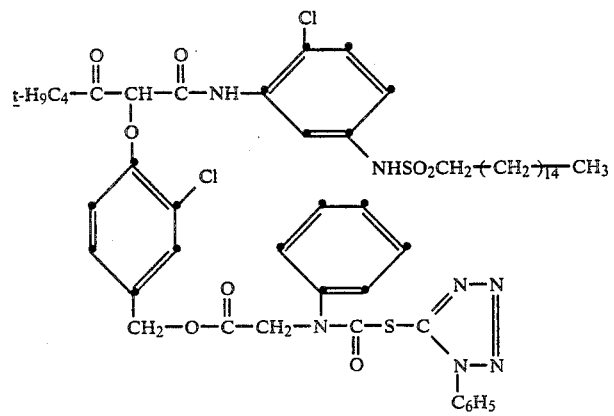
Coupler 5
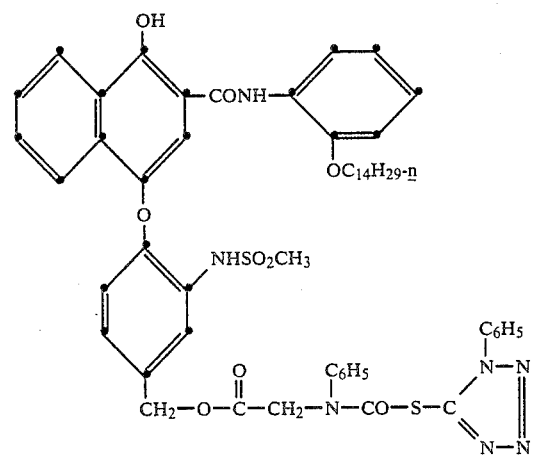
Coupler 6
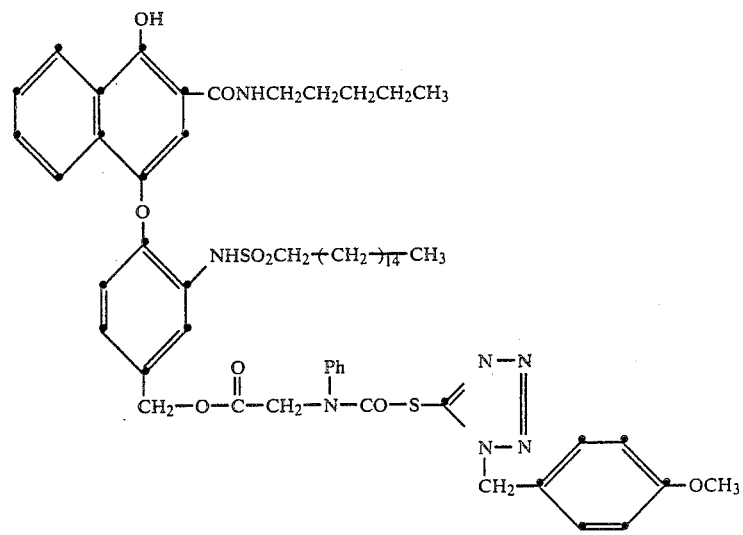
Coupler 7

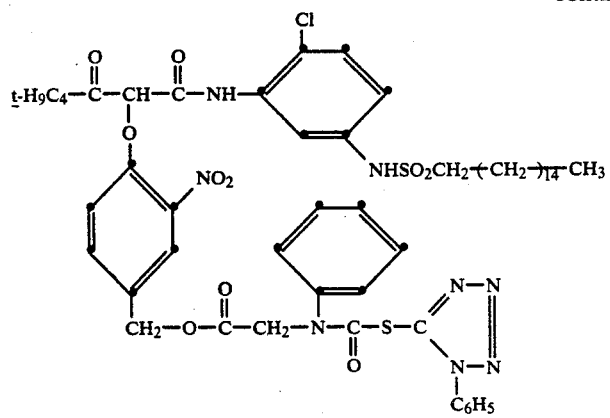
Coupler 8
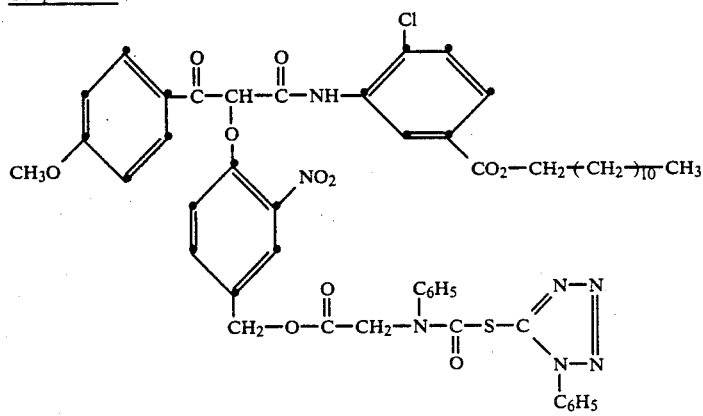
Coupler 9
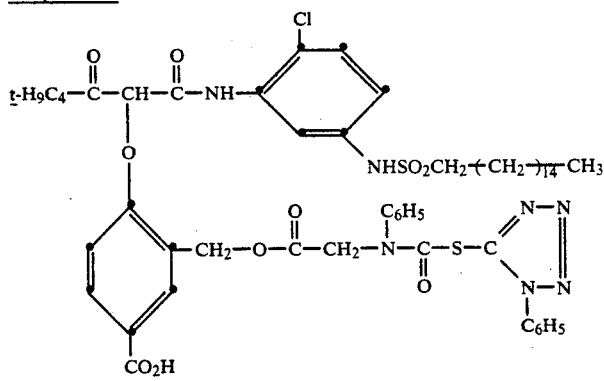
Coupler 10
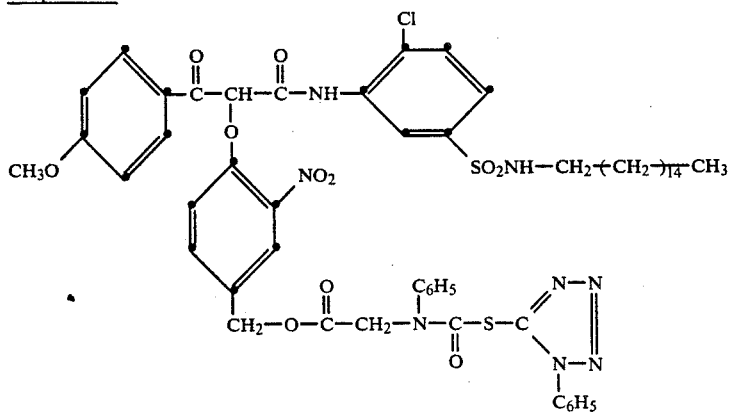

Coupler 11

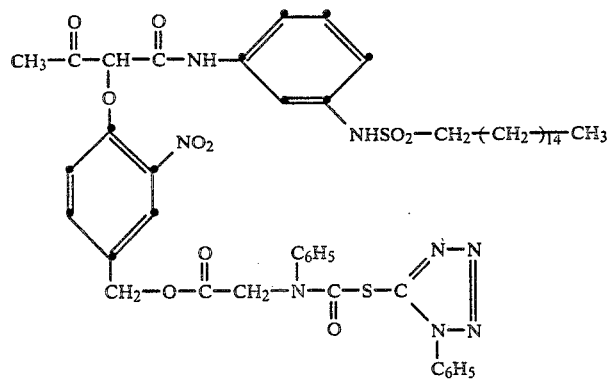

Coupler C-1 (Comparison)

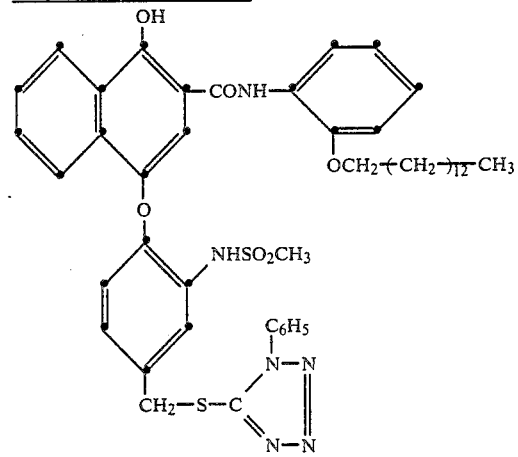

Coupler C-2 (Comparison)

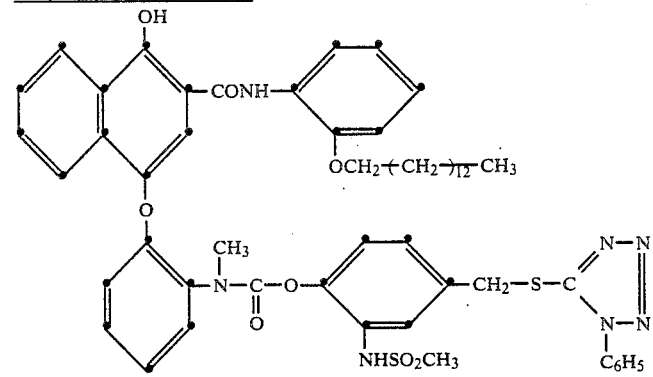

It can be seen from the interimage effects and AMT values in Table I that the use in photographic silver halide elements of couplers of the invention, which contain the described combination of groups, leads to improved sharpness compared to closely related compounds that do not contain such a combination of groups.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer and at least one development inhibitor releasing compound (A) represented by the formula CAR—LIN-K—Q where CAR is a carrier moiety capable of releasing LINK—Q during photographic processing upon reaction with oxidized developing agent; LINK—Q is in turn capable of releasing a development inhibitor group (Q) by a displacement reaction; and LINK—Q is represented by the formula:

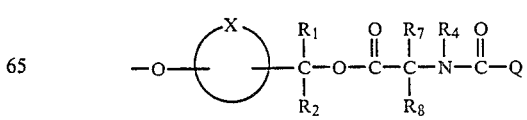

wherein

X represents the atoms necessary to complete an unsubstituted or substituted arylene or heterocyclic group;

$R_1$ and $R_2$ individually are hydrogen or unsubstituted or substituted alkyl, aryl, or together complete a 5-, 6- or 7-member ring;

$R_7$ and $R_8$ individually are hydrogen, alkyl or aryl or together complete a ring;

$R_4$ is hydrogen, unsubstituted or substituted alkyl, cycloalkyl, heterocyclic, or aryl; and Q is a releasable development inhibitor group.

2. A photographic element as in claim 1 wherein the compound (A) is a dye-forming coupler.

3. A photographic element as in claim 1 wherein the LINK—Q is represented by the formula:

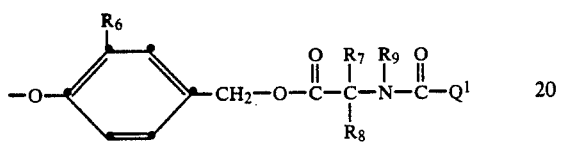

or

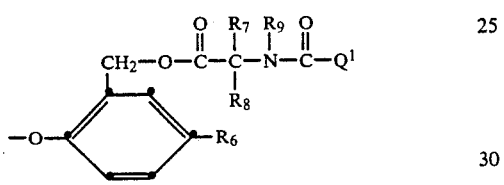

wherein $R_6$ is hydrogen, nitro (—NO₂), a substituted or unsubstituted sulfonamido group, a substituted or unsubstituted sulfamyl group, a substituted or unsubstituted carbonamido group or a substituted or unsubstituted carbamyl group;

$R_7$ and $R_8$ individually are hydrogen, unsubstituted or substituted alkyl or unsubstituted or substituted aryl or together complete a ring;

$R_9$ is hydrogen, unsubstituted or substituted alkyl, cycloalkyl, heterocyclic or aryl; and $Q^1$ is a releasable development inhibitor group.

4. A photographic element as in claim 1 wherein the LINK—Q is

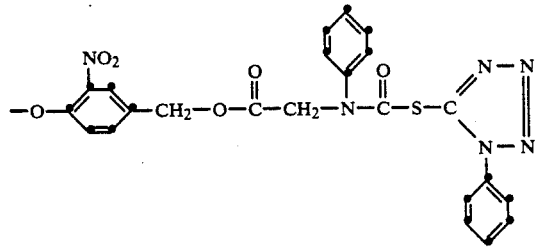

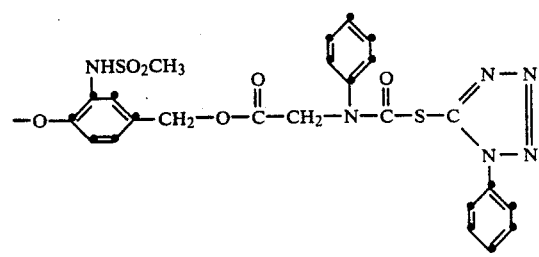

-continued

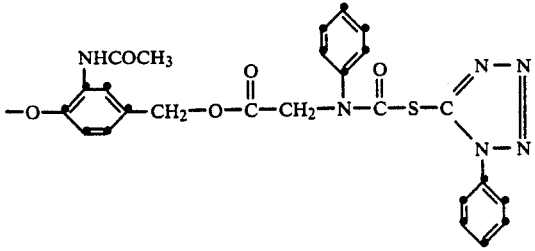

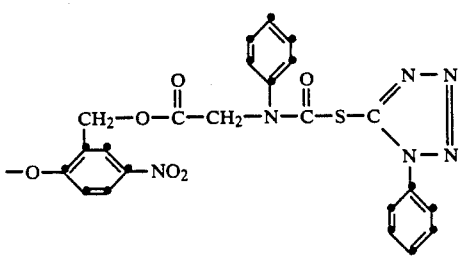

or

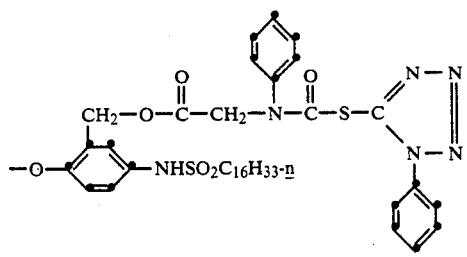

5. A photographic element as in claim 1 wherein compound (A) is represented by the formula:

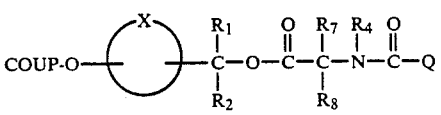

wherein

COUP is a coupler moiety;

X represents the atoms necessary to complete an unsubstituted or substituted arylene or heterocyclic group;

$R_1$ and $R_2$ individually are hydrogen or unsubstituted or substituted alkyl, aryl, or together complete a 5-, 6- or 7-member ring;

$R_7$ and $R_8$ individually are hydrogen, alkyl or aryl or together complete a ring;

$R_4$ is hydrogen, unsubstituted or substituted alkyl, cycloalkyl, heterocyclic or aryl; and, Q is a releasable development inhibitor group.

6. A photographic element as in claim 1 wherein the compound (A) is

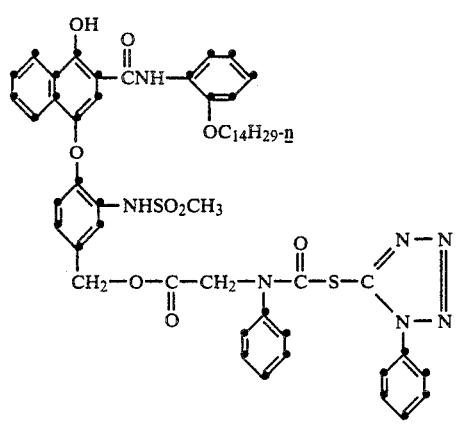
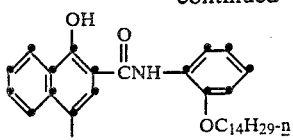
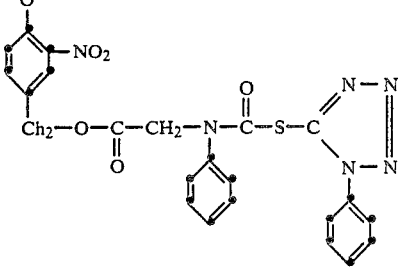
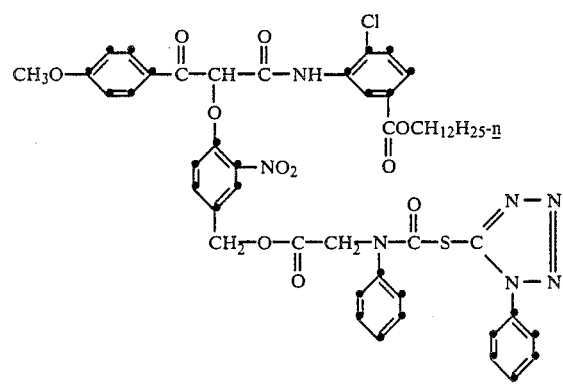
or
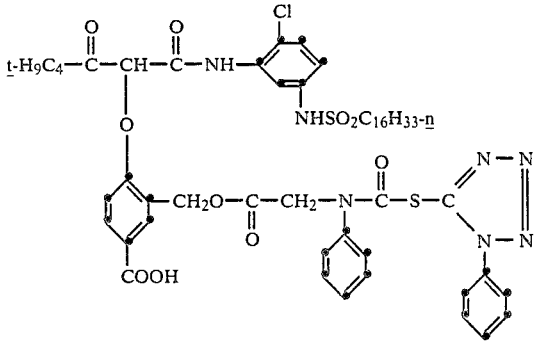
* * * * *